United States Patent
Lovell et al.

(10) Patent No.: US 7,210,481 B1
(45) Date of Patent: May 1, 2007

(54) NOSE MASK

(75) Inventors: John R. Lovell, Edgewater, NJ (US); Paul R. Chiesa, Candia, NH (US); Thomas M. Moulton, Hampton, NH (US)

(73) Assignee: SleepNet Corporation, Manchester, NH (US)

( * ) Notice: Subject to any disclaimer, the term of this patent is extended or adjusted under 35 U.S.C. 154(b) by 0 days.

(21) Appl. No.: 09/979,972

(22) PCT Filed: May 26, 2000

(86) PCT No.: PCT/US00/14524

§ 371 (c)(1), (2), (4) Date: Nov. 28, 2001

(87) PCT Pub. No.: WO00/74758

PCT Pub. Date: Dec. 14, 2000

(51) Int. Cl.
- *A62B 18/02* (2006.01)
- *A62B 18/08* (2006.01)
- *A61M 15/08* (2006.01)

(52) U.S. Cl. .......................... 128/205.25; 128/206.24; 128/207.18

(58) Field of Classification Search ................ 128/201.22–201.24, 204.18, 205.25, 205.27–207.18
See application file for complete search history.

(56) References Cited

U.S. PATENT DOCUMENTS

| | | | |
|---|---|---|---|
| 428,592 A | 5/1890 | Chapman | |
| 1,206,045 A | 11/1916 | Smith | |
| 1,610,793 A | 12/1926 | Kaufman | |
| 1,632,449 A * | 6/1927 | McKessson | 128/206.24 |
| 2,248,477 A | 7/1941 | Lombard | |
| 2,254,854 A | 9/1941 | O'Connell | |
| 2,376,871 A | 5/1945 | Fink | |
| D156,060 S | 11/1949 | Wade | |
| D161,337 S | 12/1950 | Hill | |
| 2,540,567 A | 2/1951 | Bennett | |
| 2,625,155 A | 1/1953 | Engelder | |
| 2,693,178 A | 11/1954 | Gilroy | |
| 2,818,861 A * | 1/1958 | Russell | 128/206.24 |
| 2,837,090 A | 6/1958 | Bloom et al. | |
| 2,868,196 A | 1/1959 | Stampe | |
| 2,902,033 A | 9/1959 | Galleher, Jr. | |
| 2,917,045 A | 12/1959 | Schildknecht et al. | |

(Continued)

FOREIGN PATENT DOCUMENTS

CA 618807 4/1961

(Continued)

OTHER PUBLICATIONS

Healthdyne® Technologies Soft Series™ Mask advertisement, 1 page, undated.

(Continued)

*Primary Examiner*—Glenn K. Dawson
(74) *Attorney, Agent, or Firm*—Devine, Millimet & Branch, P.A.; Paul C. Remus

(57) ABSTRACT

A nasal mask (301) includes a shell (308) forming a chamber (390) having an inlet (332) and at least one outlet and a seal (302). The seal (302) is disposed proximate the outlet for contacting and sealing with external skin proximate at least one naris at a base of a nose of a user donning the mask. Substantially all of the sealing occurs between the seal (302) and the external skin.

12 Claims, 12 Drawing Sheets

U.S. PATENT DOCUMENTS

| | | | |
|---|---|---|---|
| 2,931,356 A | 4/1960 | Schwarz | |
| 3,042,035 A | 7/1962 | Coanda | |
| 3,117,574 A | 1/1964 | Replogle | |
| 3,288,138 A | 11/1966 | Sachs | |
| 3,315,672 A | 4/1967 | Cunningham et al. | |
| 3,330,273 A | 7/1967 | Bennett | |
| 3,725,953 A * | 4/1973 | Johnson et al. | 2/14 |
| 4,062,357 A | 12/1977 | Laerdal | |
| D248,497 S | 7/1978 | Slosek | |
| 4,167,185 A | 9/1979 | Lewis | |
| 4,201,205 A | 5/1980 | Bartholomew | |
| 4,226,234 A | 10/1980 | Gunderson | |
| 4,231,363 A | 11/1980 | Grimes | |
| 4,266,540 A | 5/1981 | Panzik et al. | |
| 4,337,767 A | 7/1982 | Yahata | |
| 4,354,488 A | 10/1982 | Bartos | |
| 4,369,284 A | 1/1983 | Chen | |
| 4,412,537 A | 11/1983 | Tiger | |
| 4,414,973 A | 11/1983 | Matheson et al. | |
| 4,417,575 A | 11/1983 | Hilton et al. | |
| 4,446,576 A | 5/1984 | Hisataka | |
| 4,454,880 A | 6/1984 | Muto et al. | |
| 4,458,679 A | 7/1984 | Ward | |
| 4,572,323 A | 2/1986 | Randall | |
| 4,593,688 A | 6/1986 | Payton | |
| D285,496 S | 9/1986 | Berman | |
| 4,655,213 A * | 4/1987 | Rapoport et al. | 128/205.25 |
| 4,665,570 A | 5/1987 | Davis | |
| 4,674,134 A | 6/1987 | Lundin | |
| 4,707,863 A | 11/1987 | McNeal | |
| 4,770,169 A | 9/1988 | Schmoegner et al. | |
| 4,782,832 A | 11/1988 | Trimble et al. | |
| 4,799,477 A | 1/1989 | Lewis | |
| 4,799,526 A * | 1/1989 | Reeves | 160/168.1 R |
| 4,807,617 A | 2/1989 | Nesti | |
| 4,811,730 A | 3/1989 | Milano | |
| 4,856,118 A | 8/1989 | Sapiejewski | |
| D304,384 S | 10/1989 | Derobert | |
| 4,915,106 A | 4/1990 | Aulgur et al. | |
| 4,919,128 A * | 4/1990 | Kopala et al. | 128/207.18 |
| 4,944,310 A | 7/1990 | Sullivan | |
| D310,431 S | 9/1990 | Bellm | |
| 4,960,121 A | 10/1990 | Nelson et al. | |
| 4,971,051 A | 11/1990 | Toffolon | |
| 4,989,271 A | 2/1991 | Sapiejewski et al. | |
| 5,003,631 A | 4/1991 | Richardson | |
| 5,003,633 A | 4/1991 | Itoh | |
| 5,018,519 A | 5/1991 | Brown | |
| 5,074,297 A | 12/1991 | Venegas | |
| 5,093,940 A | 3/1992 | Nishiyama | |
| 5,109,839 A | 5/1992 | Blasdell et al. | |
| 5,138,722 A | 8/1992 | Urella et al. | |
| 5,146,914 A | 9/1992 | Sturrock | |
| 5,181,506 A | 1/1993 | Tardiff, Jr. et al. | |
| 5,199,424 A | 4/1993 | Sullivan et al. | |
| D335,322 S | 5/1993 | Jones | |
| 5,243,971 A | 9/1993 | Sullivan et al. | |
| 5,245,995 A | 9/1993 | Sullivan et al. | |
| 5,269,296 A | 12/1993 | Landis | |
| 5,331,691 A | 7/1994 | Runckel | |
| 5,334,646 A | 8/1994 | Chen | |
| 5,343,878 A | 9/1994 | Scarberry et al. | |
| 5,349,949 A | 9/1994 | Schegerin | |
| 5,390,373 A | 2/1995 | Flory | |
| 5,400,781 A | 3/1995 | Davenport | |
| 5,429,683 A | 7/1995 | Le Mitouard | |
| 5,477,852 A | 12/1995 | Landis et al. | |
| 5,485,837 A | 1/1996 | Soles Bee et al. | |
| 5,511,541 A | 4/1996 | Dearstine | |
| 5,517,986 A | 5/1996 | Starr et al. | |
| 5,522,382 A | 6/1996 | Sullivan et al. | |
| 5,540,223 A | 7/1996 | Starr et al. | |
| RE35,339 E | 10/1996 | Rapoport | |
| 5,560,354 A | 10/1996 | Berthon-Jones et al. | |
| 5,570,684 A | 11/1996 | Behr | |
| 5,592,938 A | 1/1997 | Scarberry et al. | |
| 5,617,849 A | 4/1997 | Springett et al. | |
| 5,645,054 A | 7/1997 | Cotner et al. | |
| 5,647,357 A * | 7/1997 | Barnett et al. | 128/206.24 |
| 5,657,752 A | 8/1997 | Landis et al. | |
| 5,660,174 A | 8/1997 | Jacobelli | |
| 5,662,101 A | 9/1997 | Ogden et al. | |
| D385,960 S | 11/1997 | Rudolph | |
| 5,704,345 A | 1/1998 | Berthon-Jones | |
| 5,724,965 A * | 3/1998 | Handke et al. | 128/207.13 |
| 5,740,795 A | 4/1998 | Brydon | |
| 5,746,201 A | 5/1998 | Kidd | |
| D398,987 S | 9/1998 | Cotner et al. | |
| D402,755 S | 12/1998 | Kwok | |
| RE36,165 E | 3/1999 | Behr | |
| 5,884,624 A | 3/1999 | Barnett et al. | |
| 5,896,857 A | 4/1999 | Hely et al. | |
| 5,921,239 A * | 7/1999 | McCall et al. | 128/205.25 |
| 5,966,745 A | 10/1999 | Schwartz et al. | |
| 6,006,748 A | 12/1999 | Hollis | |
| D419,658 S | 1/2000 | Matchett et al. | |
| D421,298 S | 2/2000 | Kenyon et al. | |
| 6,019,101 A | 2/2000 | Cotner et al. | |
| 6,029,660 A | 2/2000 | Calluaud et al. | |
| 6,029,665 A | 2/2000 | Berthon-Jones | |
| D423,096 S | 4/2000 | Kwok | |
| 6,044,844 A | 4/2000 | Kwok et al. | |
| 6,091,973 A | 7/2000 | Colla et al. | |
| D428,987 S | 8/2000 | Kwok | |
| 6,098,205 A | 8/2000 | Schwartz et al. | |
| 6,112,746 A | 9/2000 | Kwok et al. | |
| 6,152,137 A | 11/2000 | Schwartz et al. | |
| 6,176,538 B1 * | 1/2001 | Lawson et al. | 296/78.1 |
| 6,192,886 B1 * | 2/2001 | Rudolph | 128/207.13 |
| 6,196,223 B1 * | 3/2001 | Belfer et al. | 128/206.25 |
| 6,631,718 B1 * | 10/2003 | Lovell | 128/206.24 |

FOREIGN PATENT DOCUMENTS

| | | |
|---|---|---|
| CA | 623129 | 7/1961 |
| DE | 42 12 259 | 1/1993 |
| DE | 195 48 380 | 7/1996 |
| DE | 198 07 961 | 8/1999 |
| EP | 0 549 299 | 6/1993 |
| EP | 0 747 078 | 12/1996 |
| FR | 780018 | 4/1935 |
| FR | 2 658 725 | 8/1991 |
| FR | 2 720 280 | 12/1995 |
| FR | 2 749 176 | 12/1997 |
| WO | 93/24169 | 12/1993 |
| WO | 97/09090 | 3/1997 |
| WO | 98/18514 | 5/1998 |
| WO | 98/48878 | 11/1998 |
| WO | 99/43375 | 9/1999 |
| WO | 99/58181 | 11/1999 |

OTHER PUBLICATIONS

Lifecare® Form #544, 1 page, (Jul. 1991).
Medical Industries America Universal Deluxe C.P.A.P. Headgear advertisement, 1 page, undated.
Puritan Bennett Companion® Nasal CPAP Masks advertisement, 1 page, undated.
ResCare Sullivan® Bubble Mask™ System Series 3 advertisement, 3 pages, undated.
Respironics Inc. Monarch Mini Mask information sheet, 1 page, (Feb. 26, 1996).
Respironics Inc. Pamphlet, "Profile™ Custom Nasal Mask Instructions for Use," (Dec. 14, 1998).

Smith et al., "Indications and Standards for Use of Nasal Continuous Positive Airway Pressure (CPAP) in Sleep Apnea Syndromes," *Am. J. Respir. Crit. Care Med.*, vol. 150, pp. 1738-1745 (1994).

Vital Signs, Inc. Pamphlet, "SoftNair™" (1998).

American Society for Testing and Materials (ASTM) "Designation D 2240-97[e1] : Standard Test Method for Rubber Property—Durometer Hardness," pp. 1-4, (approved Feb. 10, 1997, updated Feb. 1999).

Barracuda The Best Swim Goggles Packaging, 1 page (date unknown).

Parker Laboratories, Inc., Aquaflex® Ultrasound Gel Pad sales literature, 1 page, (1991).

3M Health Care sales brochure, "Just plain talk about the many uses of Tegaderm™ transparent dressing," 12 pages (1990).

* cited by examiner

NOSE MASK

This application is the national phase of International (PCT) Patent Application Ser. No. PCT/US00/14524, filed May 26, 2000, published under PCT Article 21(2) in English, which claims priority to U.S. Ser. No. 09/328,120 and U.S. Ser. No. 09/328,027, both filed Jun. 8, 1999. The entire disclosures of these three applications are incorporated herein by reference.

TECHNICAL FIELD

The present invention relates to respiratory apparatus and more specifically to a nasal mask useful for providing pressurized air or therapeutic gas to a patient suffering from an airflow limitation or other respiratory ailment.

BACKGROUND INFORMATION

Patients suffering from a variety of medical conditions often require supplementary respiratory support. Depending on the nature and severity of the condition, this respiratory support can range from providing an elevated oxygen concentration cloud to the vicinity of the nose and mouth, to forcing ventilation of the lungs by intubating the trachea. In general, a supply of pressurized air or therapeutic gas is provided by a tube or conduit to a delivery apparatus designed to conform to particular body structure.

One style of delivery apparatus is a mask which provides the gas to a nasal area of the patient. Nasal masks are often employed in the treatment of sleep apnea syndrome, characterized by intermittent upper airway obstruction during sleep. Due to the resulting blood oxygen desaturation and frequent arousals from sleep, persons suffering from this condition are often unable to achieve deep sleep for extended periods, are chronically tired, and are physically compromised.

Because nasal masks are often worn by persons in unmonitored environments for extended periods, such as in the home during sleep, the nasal mask should be comfortable to wear and conform well to the nasal area. If the mask is deemed too bulky, too heavy, or to fit poorly, the patient will either not wear the mask, wear the mask improperly, or only wear the mask occasionally when the discomfort associated with the respiratory condition exceeds the discomfort of wearing the mask.

One problem associated with nasal masks relates to the conformance of the mask to the nasal area, which is complexly contoured and differs from patient to patient. Customized masks manufactured to suit particular patients tend to be costly; therefore, masks for general use are typically made in several generic sizes, each size designed to accommodate a range of patients. If the mask does not form a good seal around the patient's nose, leakage can occur, reducing the effectiveness of the treatment. When poorly fitting masks are used with variably regulated air supply systems responsive to patient breathing, such as those developed for treating sleep apnea, mask leakage can induce improper system response which may exacerbate the patient's condition. Regulated air supply systems and delivery apparatus for treatment of sleep apnea are disclosed in Patent Cooperation Treaty international application number PCT/US93/05095, published on Dec. 9, 1993, as international publication number WO 93/24169; U.S. patent application Ser. No. 08/184,976 filed Jan. 24, 1994; U.S. Pat. No. 5,199,424; U.S. Pat. No. 5,245,995; U.S. Pat. No. 5,522,382; U.S. Pat. No. 5,645,054; U.S. Pat. No. 6,019,101; and U.S. Des. Pat. No. D398,987, the disclosures of all of which are herein incorporated by reference.

One method of reducing leakage is to provide a compliant sealing flange or surface around a perimeter of the mask in combination with a strap to bias the mask into sealing engagement with the nasal contour of the patient. Typically, the greater the retention force applied by the strap, the better the seal; however, both the strap and the mask can cause excessive pressure on delicate areas, resulting in irritation and patient discomfort.

The retention force required to prevent leakage is also a function of forces and torques induced in the mask. For example, the weight of the conduit supplying air or gas to the mask tends to pull the mask downward, away from the patient's nasal area, when the patient is sitting. Additionally, any movement of the head from side-to-side or up and down can cause lifting of an edge or sliding of the mask and strap. The more rapid the movement, the more pronounced the effect. Mask slippage and displacement are exacerbated in masks employing large diameter, heavy, or stiff tubes which deliver relatively large volumetric flow rates of air, such as those employed in sleep apnea treatment systems.

For nasal masks used by patients when sleeping, the strap and seal arrangement should also accommodate unconscious or reflexive head and body movements. The discomfort associated with masks which apply too much pressure to the head, neck, or nasal area discourage use of the mask during sleep when it is most needed. As a result, treatment is compromised and the patient is ill served by the apparatus.

Accordingly, there exists a need to overcome the limitations of known designs by providing an improved nasal mask which provides a consistent, reliable nasal area seal while being comfortable to wear. Other desirable features would include ease of manufacture and low cost.

SUMMARY OF THE INVENTION

Devices of the present invention allow for comfortable delivery of a breathable gas to a user. More particularly, devices of the invention seal with the external skin surrounding the nares at the base of the nose and/or along the inner rim of the nares of a user. The seal is both comfortable for the patient and reliable. Both the softness of a gel seal according to the invention and the design of devices according to the invention which invite minimal contact between the user's epidermal areas and the device, combine to create this comfortable and reliable seal about the user's nares.

In one aspect of the invention a nasal mask includes a shell and a first seal. The shell forms a chamber having an inlet and at least one outlet. The first seal is disposed proximate the outlet for contacting and sealing with external skin proximate at least one naris at a base of a nose of a user donning the mask. Substantially all of the sealing occurs between the seal and the external skin.

Certain embodiments of this aspect of the invention may include any or all of the following features. A nasal mask can include both a second seal and a second outlet. The first seal can be integral with the second seal. The nasal mask also can include a malleable element disposed within the shell. Additionally, a seal of a nasal mask can include a bladder. The bladder can be filled with silicone gel, molded in a predetermined configuration, and/or bonded to the shell.

A conduit can be attached to the inlet of a nasal mask. The conduit can include an angled portion, a rotary connection, and/or a ball and socket connection. Additionally, the conduit can have a side wall defining a lumen within the side wall. The side wall can contain at least one opening in communication with the lumen.

A headgear apparatus can be attached to the mask for retaining the mask on a user. A retainer can be disposed about the inlet and cooperate with the headgear apparatus to retain the mask on a user. One or more connectors can attach the headgear apparatus to the mask. One or more of the connectors can attach to the retainer.

Another aspect of the invention includes a system for treating a respiratory ailment in a recumbent or sleeping user. The system includes a nasal mask as described above connected to a controlled, breathable gas source with a conduit. The nasal mask may include any of the features described above.

Another aspect of the invention comprises a seal for use with a nasal mask including a bladder filled with a molded material in a predetermined configuration. The material has a durometer value less than about ten on a Shore OOO scale. The seal is configured typically with a slight crown to seal against external skin proximate at least one naris at a base of a nose of a user. The material can be silicone.

The bladder can have at least one protrusion on a side thereof for contacting the external skin proximate at least one naris at a base of a nose of a user and/or can be substantially planar on a side thereof for contacting a shell of the nasal mask. The seal can have a thickness and can form at least one aperture therethrough disposable proximate a naris. A thickness of the bladder proximate the aperture can be less than a thickness of the seal remote therefrom.

BRIEF DESCRIPTION OF THE DRAWINGS

The invention, in accordance with preferred and exemplary embodiments, together with further advantages thereof, is more particularly described in the following detailed description, taken in conjunction with the accompanying drawings.

In the drawings, like reference characters generally refer to the same parts throughout the different views. Also, the drawings are not necessarily to scale, emphasis instead generally being placed upon illustrating principles of the invention.

DESCRIPTION

Figure 1A:
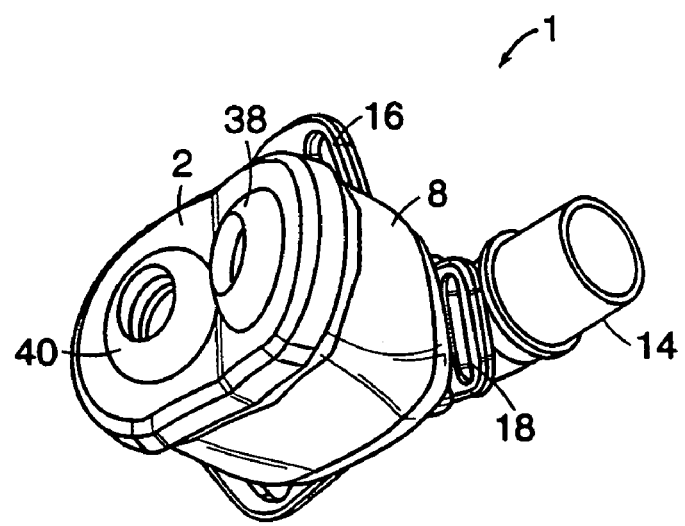
FIG. 1A is a schematic perspective view of one embodiment of the invention.
Figure 1B:
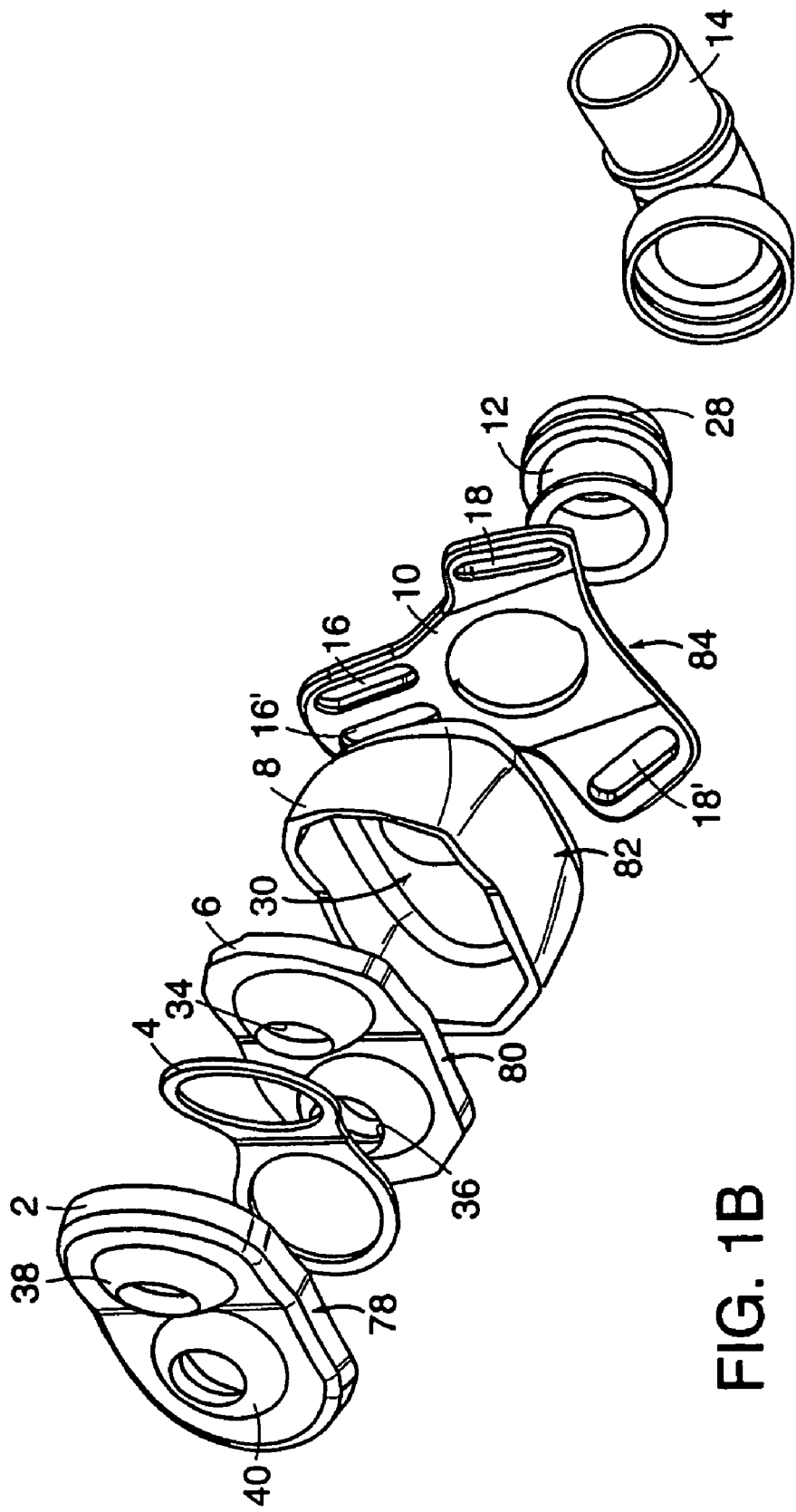
FIG. 1B is a schematic exploded perspective view of the embodiment of FIG. 1A.

The present invention provides a comfortable, reliably sealing nasal mask for delivering a breathable gas to a user. In particular a seal bonded to a shell of the nasal mask is particularly soft. This seal rests comfortably on the external skin surrounding the nares at the base of the nose and/or along the inner rim of the nares of a user.

The design of nasal masks according to this invention provides solutions to several common problems with current designs. First, the nasal mask's contact with the user's face is minimal compared with current masks. Second, the seal distributes contact pressure, unlike many current masks. Third, the design allows the user to comfortably lie in almost any position. Fourth, the design provides a comfortable fit and a reliable seal for a wide range of the population compared with many current masks which either must be stocked in multiple sizes or simply do not properly fit on users with faces of a certain shape.

Referring to FIGS. 1A–4B, in one embodiment of a nasal mask 1 depicted in a variety of orientations, a seal 2 covers an upper shell 6. Typically, the seal 2 is bonded to at least a portion of the upper shell 6. Useful bonding agents include, but are not limited to, tetrahyrdofuran ("THF") and/or ultraviolet cured adhesives. Alternative attachment methods are acceptable. For example, mechanically interlocking features, such as a tapered dovetail or flange, could be employed with mating recesses. A malleable element 4 is typically disposed within the upper shell 6 by a process such as, but without limitation, injection molding the upper shell 6 around the malleable element 4. Alternatively, the malleable element 4 can be disposed within a lower shell 8, disposed on the surface of the upper shell 6, and/or disposed between the upper shell 6 and lower shell 8.

The upper shell 6 is contoured such that two outlets 34, 36 protrude from it symmetrically along its mid-line. The malleable element 4 has holes in it that correspond to and are disposed around the outlets 34, 36 in the upper shell 6. The lower portion of a shell 8 is affixed to the upper portion of the shell 6. The two portions of the shell, for example, but without limitation, can be heated and welded together, welded together with a solvent and/or bonded together with a bonding agent. The shell portions 6, 8 typically, are manufactured from a flexible material, for example, but without limitation, by a molding process using a compliant polymer. Each of the two portions of the shell, for example, but without limitation, can be manufactured from a thermopolymer elastomer. A flange 42 seats the upper shell 6 securely on the lower shell 8 and allows for a larger surface area for affixing the upper shell 6 to the lower shell 8. The combination of the upper and lower shells 6, 8 produces a chamber 30. When in communication with a source of breathable gas, this chamber 30 contains the breathable gas. The gas in the chamber 30 is available to the user donning the nasal mask, and the gas, typically, is pressurized such that the gas is forced into the user's airway, holding open the airway. The chamber 30 is substantially leakage-free due to the bond between the seal 2 and the upper shell 6 (or other attachment methods) and the compliance of the seal 2 against a user's skin The malleable element 4 is a double ring of a soft metal. Alternatively, the malleable element 4 can be constructed from any material that is formable and is capable of retaining the shape into which it is formed against the force of, for example, the flexible shell portions 6, 8 trying to regain their memory shape. The combination of the compliant and resilient shell portions 6, 8 and the malleable element 4 with sufficient rigidity to hold the shell portions 6, 8 in a selected configuration produces a "custom-fit" as desired by a particular user. Because the shell portions 6, 8 are resilient, the shell portions 6, 8 can be reformed any number of times as desired by a particular user. Typically, a user will adjust the fit of nasal mask 1 by bending the nasal mask 1 along its mid-line and the mid-line of the malleable element 4 contained within the nasal mask 1 into a "V" shape, as shown for example, in FIG. 8B. Bending the malleable element 4 in this manner adjusts the fit of the outlets 34, 36 and complementary domes 38, 40 of the seal 2, which overlie the outlets 34, 36, to the external skin of the nares of a user donning a nasal mask, including the inner rim of the nares. The midline can be seen, for example, as line A—A in FIG. 4A. Increasing the pitch of a side of the "V" will move the particular outlet and complementary dome closer to the other outlet and complementary dome, while decreasing the pitch of a side of the "V" will move the particular outlet and complementary dome away from the other outlet and complementary dome. Additionally, the malleable element 4 can be bent in other directions, allowing the nasal mask 1 to be formed into a variety of configurations.

The nasal mask 1 includes an inlet 32 into which a swivel connector 12 fits. The swivel connector 12 has a slightly concave shape on the end that fits into the inlet 32. A conduit elbow 14 fits onto the swivel connector 12 over a flange 28 on the swivel connector 12. The connection between the inlet 32 and the swivel connector 12 and/or the connection between the swivel connector 12 and the conduit elbow 14 can be a permanent and inseparable connection or the connection can be a selectively removable connection. The swivel connector 12 produces a swivel mount connection between the conduit elbow 14 and the inlet 32. In this type of connection, the conduit elbow 14 is capable of being rotated 360 degrees about an axis extending through the center of the inlet 32. In an alternative embodiment, the connection is characterized by a ball and socket connection. In this alternative type of connection, the conduit elbow has a second angular degree of freedom in addition to the single rotational degree of freedom of the swivel mount connection. The conduit elbow 14 may be manufactured from, for example, but without limitation to, polycarbonate. The swivel connector 12 also can be manufactured from, for example, but without limitation, polypropylene.

Figure 2A:
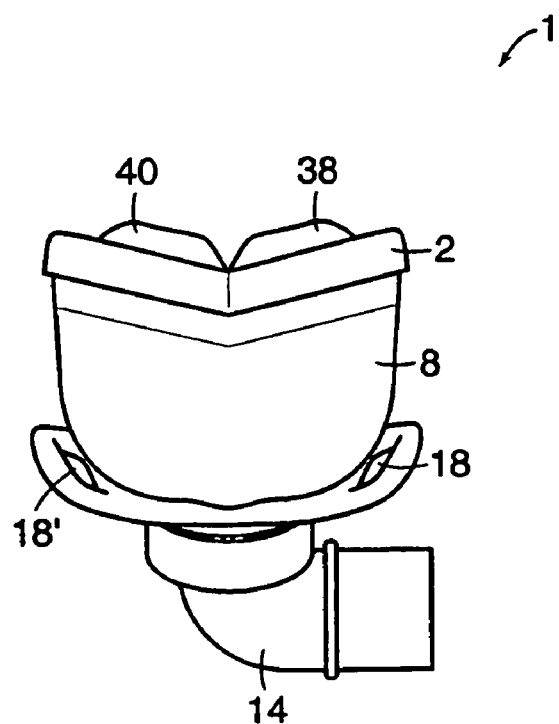
FIG. 2A is a schematic front view of the embodiment of FIG. 1A.
Figure 2B:
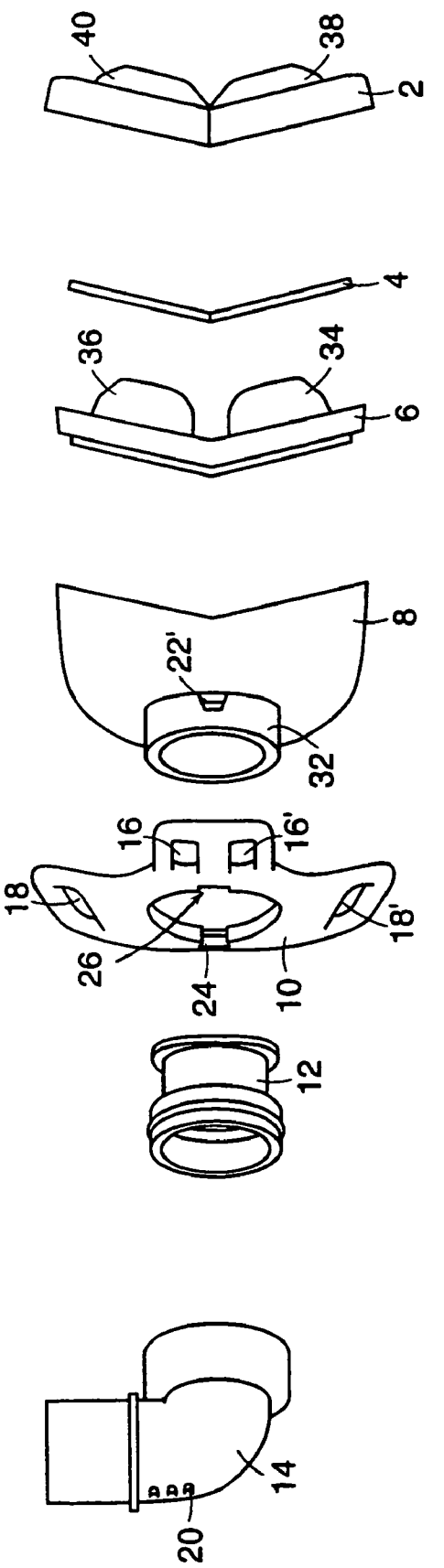
FIG. 2B is a schematic exploded front view of the embodiment of FIG. 1A.
Figure 3A:
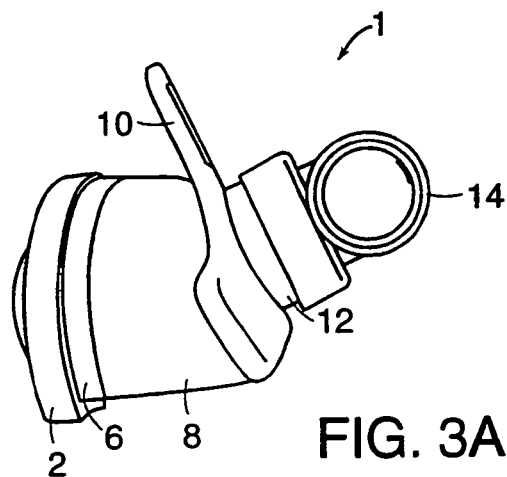
FIG. 3A is a schematic side view of the embodiment of FIG. 1A.
Figure 4A:
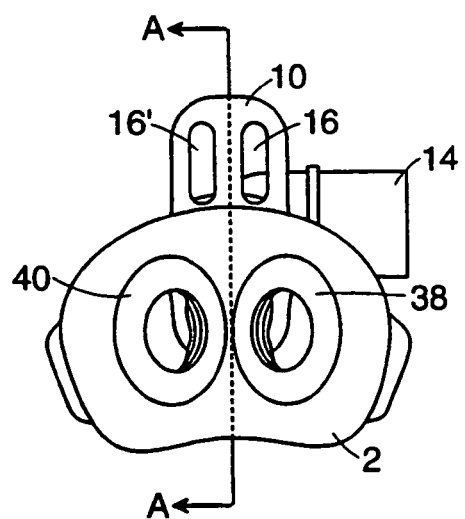
FIG. 4A is a schematic top view of the embodiment of FIG. 1A.
Figure 4B:
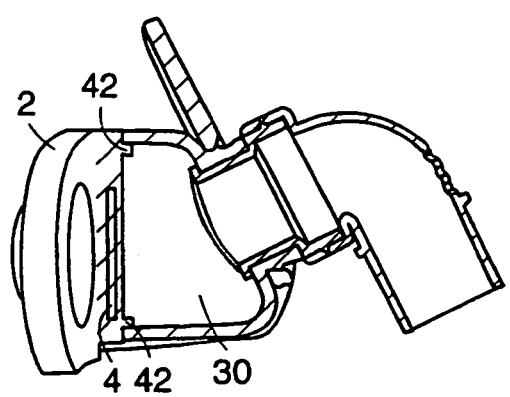
FIG. 4B is a schematic cross-sectional view of the embodiment of FIG. 1A taken along line A—A of FIG. 4A.
Figure 3B:
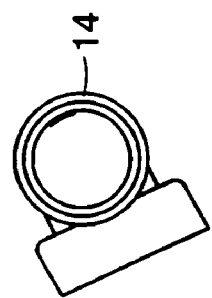
FIG. 3B is a schematic exploded side view of the embodiment of FIG. 1A.
Figure 3B:
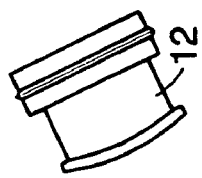
Figure 3B:
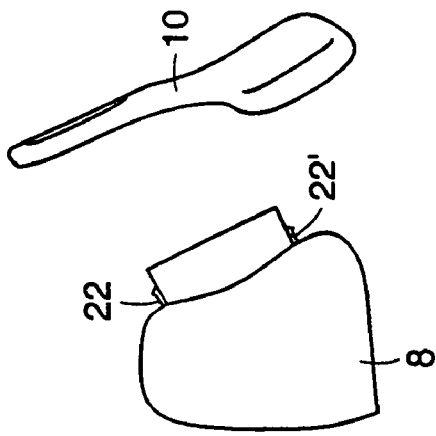
Figure 3B:
Figure 3B:
Figure 3B:

The conduit elbow 14 is shown with an angled portion of about ninety degrees, as well as apertures 20 as seen in FIG. 2B, only one aperture being labeled for the sake of clarity. These apertures 20 allow the release of gases exhaled by the user. In current hose designs, a user can be disturbed by gasses escaping from the hose through the apertures because of noise or a "blowing" sensation. The apertures 20 of this embodiment of the invention are designed to prevent escaping gases from disturbing a user. More than one aperture 20 is used (in this embodiment three apertures 20 are used) in order to diffuse the flow of exhaled gas. Additionally, the apertures 20 do not have sharp edges at their perimeter so that noise of gas moving through the apertures 20 is reduced. The apertures 20 are positioned on a remote side of the conduit elbow 14 so that gas is vented in a single direction rather than multiple directions. The nasal mask 1 can optionally include more than one inlet to allow for additional hoses and/or sources of gas to be connected. Also, one or more outlets can be included optionally to allow for drainage of any condensation formed within the chamber 30 of the shell 6, 8 and/or to attach monitoring devices such as pressure, temperature, or flow sensors.

In addition, a retainer 10 is disposed about the inlet 32. Two tabs 22, 22' included on the inlet 32 mate with two slots 24, 26, respectively, and hold the retainer 10 in a particular angular orientation. The retainer 10 has four connection points, two lower connection points 18, 18' and two upper connection points 16, 16'. Typically, the tabs 22, 22' hold the retainer 10 in an orientation such that the upper connection points 16, 16' are above the lower connection points 18, 18'. These connection points 16, 16', 18, 18' allow for connection between the retainer 10 and a headgear apparatus. The retainer 10 can be constructed from, for example, but without limitation, a polycarbonate. Alternative embodiments may have a different number of connection points and/or may have a mechanically different method of fastening a headgear apparatus to a nasal mask. Fastening devices such as, but without limitation, snaps, hook and eye closures, hook and loop fasteners, or the like, may be used.

Figure 5:
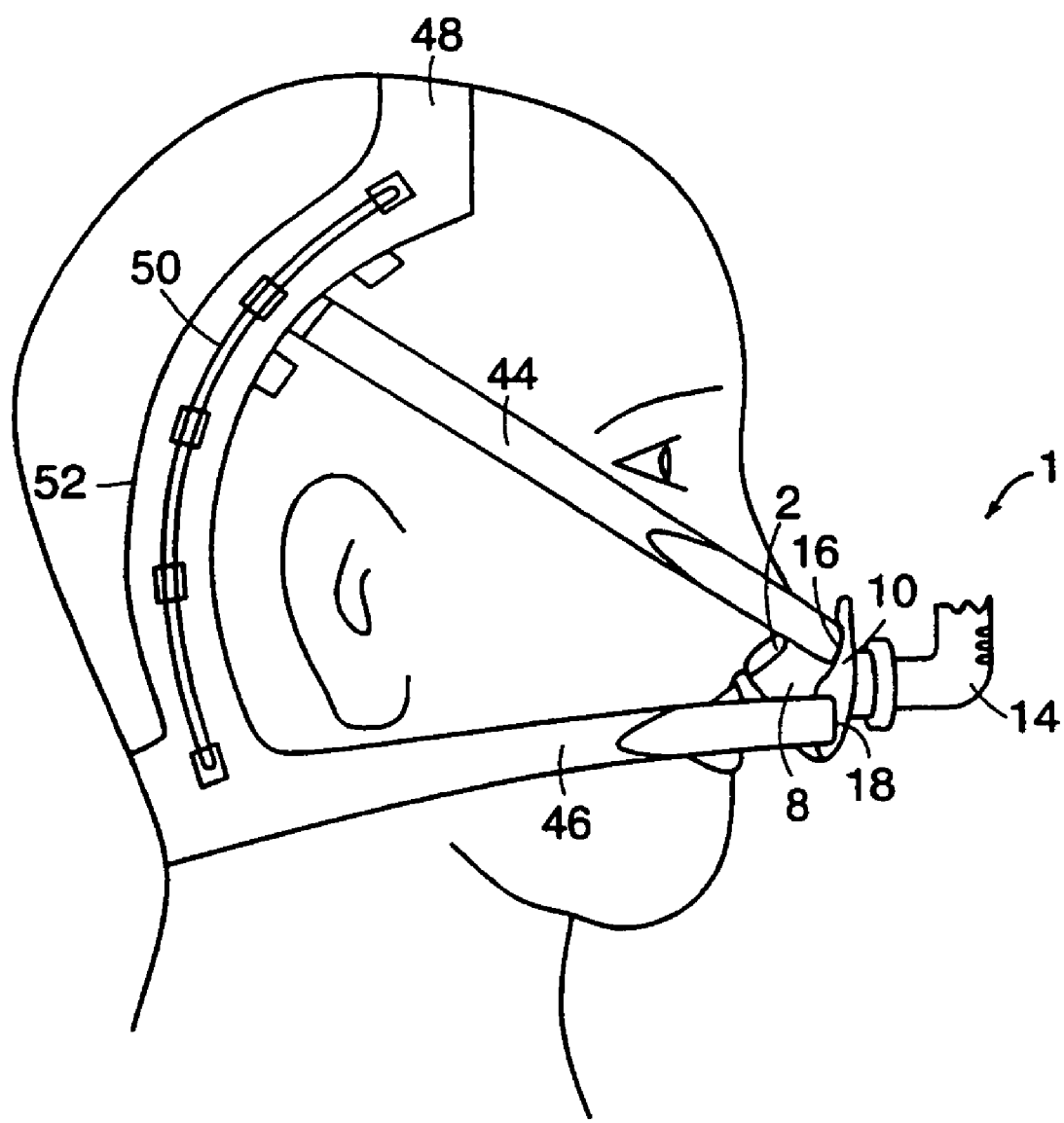
FIG. 5 shows a user donning the nasal mask of FIG. 1A.

Now referring to FIG. 5, when the nasal mask 1 is donned by a user, the nasal mask 1 is maintained on the area around a user's nares with a headgear apparatus 48. The headgear apparatus 48 is shown as straps 44, 46, 52 which rest on the head as indicated in FIG. 5. The straps 44, 46, 52 of the headgear apparatus 48 do not fall across the ears of a user. Avoiding contact between the straps 44, 46, 52 and the ears of a user increases the comfort level of a user wearing the headgear apparatus 48. The straps 44, 46, 52 may be manufactured from elastic materials such as, but not limited to, nylon webbing, nylon covered neoprene and Velstretch™, available from Velcro USA Inc., Manchester, N.H., and may further include optional padding, if desired. The headgear apparatus 48 also can be reinforced with a beam element 50 that allows the headgear apparatus 48 to retain a roughly helmet shape when not placed on the head of a user. The beam element 50 may be plastically or elastically deformable and may be manufactured, for example, from a polymer, metal, or other suitable material. According to one embodiment, the beam element may have a substantially flat cross-section, so as not to create an uncomfortable ridge if rested upon. Maintaining the helmet shape allows a user to more easily don the headgear. Those skilled in the art appreciate that other equivalent headgear apparatus configurations and headgear apparatus materials may be employed.

The headgear apparatus 48 is connected to the retainer 10. Specifically, the headgear apparatus 48 includes two upper retention straps 44, only one upper retention strap is shown, the other being hidden from view, and two lower retention straps 46, only one lower retention strap is shown, the other being hidden from view, each of which is attached to a corresponding one of two upper connection points 16, 16', only one upper connection point 16 is shown, the other 16' being hidden from view, or two lower connection points 18, 18' only one lower connection point 18 is shown, the other 18', being hidden from view, respectively. The connection points 16, 16', 18, 18' are a unitary part of the retainer 10. Modes of construction other than unitary construction will be appreciated by those skilled in the art.

This four point restraining system allows for the nasal mask 1 to be securely positioned against the nares of a user. The lower connection points 18, 18', in concert with the lower retention straps 46, generally maintain the nasal mask 1 against a user's face. The seal 2 rests against the external skin at the base of a user's nose and/or along the rim of the nares (the "naric area"). The upper connection points 16, 16' in concert with the upper retention straps 44 provide additional retention force on the upper portion of the nasal mask 1, closest to a user's eyes. This additional force retains the nasal mask 1 securely against the external skin surrounding the nares at the base of a user's nose and/or along the rim of a user's nares. The upper retention straps 44 do not block the vision of a user.

In use, a user would loop each of the lower and upper retention straps 44, 46 through each of the lower and upper connection points 16, 16', 18, 18', respectively. A hook and loop system can be used to maintain the straps 44, 46 at a desired adjustment. The loops are located along the majority of the straps 44, 46 but not at a distal tip portion of the straps 44, 46. Hooks are located on the distal tip portion such that when the distal tip of a strap is passed through a connector, the strap folds over on itself and the hooks engage the loops. Alternatively, the correct length of a strap can be adjusted and a snap on the distal tip can engage with a clip along the strap. Thus, a user only has to adjust a strap once rather than adjusting the straps each time a user dons the nasal mask.

The properly adjusted retention straps 44, 46 of the headgear apparatus 48 secure proper contact between the seal 2 and the naric area. The additional force provided by the upper connection points 16, 16' and the upper retention straps 44 ensures that the nasal mask 1 rests securely against a user's naric area during a wide range of sleeping behaviors such as entering and maintaining a preferred sleeping position or performing involuntary movements during sleep.

Figure 6:
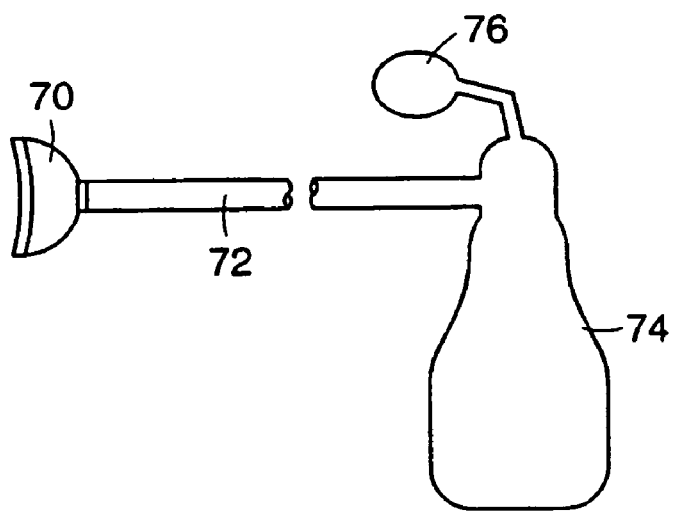
FIG. 6 shows a schematic representation of a gas source in communication with a nasal mask.

Referring to FIG. 6, a breathable gas source 74 connected to a nasal mask 70 with a conduit 72 and optionally controlled with a controller unit 76 is schematically depicted. The breathable gas source 74 could be any of a variety of configurations, including, but not limited to, a constant flow air pump, a responsive variable flow air pump, a pressure regulated oxygen tank, or the like, as discussed in the references cited hereinabove.

Figure 7:
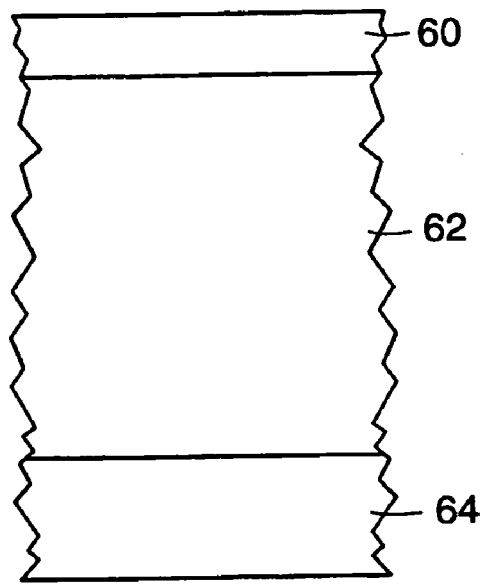
FIG. 7 is a section through one embodiment of a seal.

Now referring to FIG. 7, a section through the seal 2 is shown. Typically, the seal 2 is a bladder that is formed from a film 60, 64 and that is filled with a soft material 62. Typically, the fill material 62 has a durometer value of less than about ten on the Shore OOO scale. For example, certain types of silicone gel meet this durometer value, such as, but not limited to, molded silicone commercially available from Bragel, Inc. Pomona, Calif. as a finished product or chemical silicone constituents, such as a base and a cross-link, such as those available from Applied Silicone Corporation, Ventura, Calif., that combine to form, when cured, such a finished product.

As stated hereinabove, according to one embodiment, the seal fill material has a durometer value of less than about ten on the Shore or Type OOO scale. Such low durometer values on this scale can be measured using apparatus and test methodology generally in accordance with Type A, B, C, D, DO, O, OO durometer test method of American Society for Testing and Materials (ASTM) Designation D 2240-97$^{e1}$: Standard Test Method for Rubber Property—Durometer Hardness, approved Feb. 10, 1997, and revised editorially in February 1999, the disclosure of which is incorporated herein. As is known by those skilled in the art of testing the durometer of ultrasoft gels and sponge rubber on the Shore OOO scale, a 0.5 inch hemispherical end indentor shape is used in combination with a 113 gram-force main spring.

According to this test method, the procedure for obtaining measurements of a specimen's durometer is stated as follows:

Place the specimen on a hard, horizontal surface. Hold the durometer in a vertical position with the point of the indentor at least 12 mm (0.5 in.) from any edge of the specimen, unless it is known that identical results are obtained when measurements are made with the indentor at a lesser distance. Apply the presser foot to the specimen as rapidly as possible, without shock, keeping the foot parallel to the surface of the specimen. Apply just sufficient pressure to obtain firm contact between presser foot and specimen.

When the durometer measurement is made as stated, while maintaining sufficient pressure to maintain contact, but without permitting the presser foot of the measuring apparatus to compress the silicone gel specimen, thereby forcing a portion of the specimen into the aperture formed about the indentor and binding the indentor, reliable, repeatable readings on the Shore OOO scale can be recorded.

Furthermore, the aforementioned test method states:

NOTE 9—The type of durometer should be selected with the knowledge that readings below 10 or above 90 are not considered reliable by the manufacturer. It is suggested that readings in these ranges not be recorded.

Although readings below 10 on the Shore scale are not considered reliable by ASTM, the Shore OOO scale is the lowest scale for durometer by Shore readings. In effect, the aforementioned seal fill material is too soft for measurement by ASTM approved Shore durometer test methods. However, a reference of below ten on the Shore OOO scale measured as described hereinabove is Applicant's preferred method for characterization of the seal softness in accordance with the invention. Further, this methodology is generally known by those skilled in the art and represents industry accepted measurement standards.

The bladder itself, typically, is made from a thermopolymer material. The bladder can be formed from, for example, but not limited to, a urethane film or a polyurethane film. Urethane films are commercially available, for example, from Deerfield Urethane, Inc., Deerfield, Mass., and polyurethane films are commercially available, for example, from Elf Atochem S.A. Paris, France. The film forming the bladder can be thicker in some portions relative to other portions. For example, FIG. 7 depicts a relatively thinner portion of the film 60 and a relatively thicker portion of the film 64. Typically, the film 64 on the side of the seal that is bonded to the shell is thicker than the film 60 on the side of the seal which contacts the face of a user. In one embodiment, the seal has about a 75 μm thick urethane film on the side bonded to the shell and has about a 50 μm thick urethane film on the side which contacts the face of a user. Accordingly, when the seal 2 is bonded to the shell 6, for example with a bonding agent such as tetrahydrofuran or an ultraviolet cured adhesive, sufficient margin exists to prevent the film from being breached due to attack by the bonding agent. The film disposed against the user's skin, however, is maintained relatively thin so as not to stiffen the seal 2.

Figure 8A:
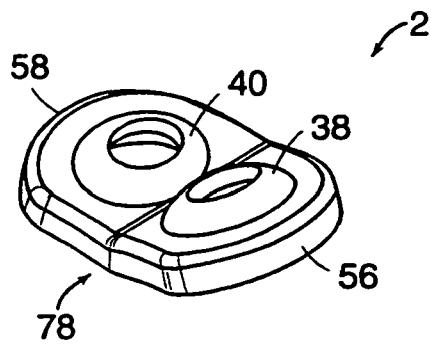
FIG. 8A is a schematic perspective view of the seal of the embodiment of FIG. 1A.
Figure 8B:
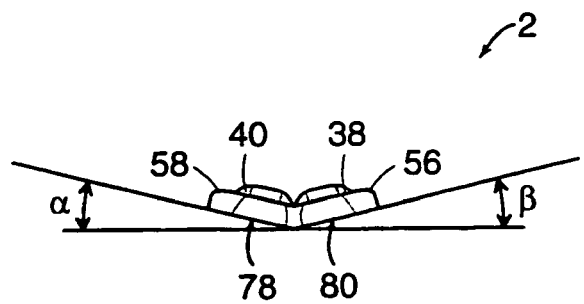
FIG. 8B is a schematic side view of the seal of FIG. 8A.
Figure 8C:
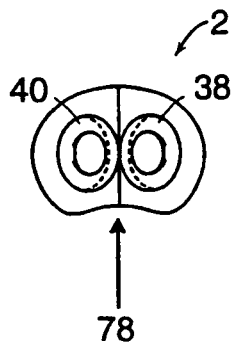
FIG. 8C is a schematic top view of the seal of FIG. 8A.

Now referring to FIGS. 8A, 8B, and 8C, the seal 2 has two domes 38, 40 that cover the two outlets 34, 36. The domes 38, 40 have a complementary space on the bonded side of the seal 2 that accepts the two outlets 34, 36. The domes in certain embodiments can protrude into the nares from about 0.1 inches to about 0.375 inches, more preferably 0.115 inches to about 0.250 inches. This depth can vary in other embodiments. Moreover, in some embodiments, the seal can seal around the inner rim of the nares. The contact, between the seal 2 and the external skin surrounding the nares at the base of the nose and/or the inner rim of the nares is minimal. Each of these domes 38, 40 are elliptical and have an elliptical opening in them that is about 0.35 inches along its short axis and 0.45 inches along its long axis. An opening in each dome 38, 40 communicates with the opening in the two outlets 34, 36, respectively. The domes 38, 40 have a generally convex sealing surface for sealing with the external skin surrounding the nares and/or along the inner rim of the nares thereby to produce an annular seal about the nares. The convex domes allow devices according to the invention to conform to the nasal area, particularly when the device is pressurized during use. The pressure further deforms the seal 2 to comply with the naric area. Thus, rather than having a device that forces the naric area to conform to the device or that extends into the nares substantially irritating the delicate mucous membrane therein, which is uncomfortable for a user, devices according to the invention conform to the naric area.

The seal 2 is about 0.225 inches thick, not including the area in which the two domes 38, 40 are located, and the seal 2 has a substantially planar side, typically the side that contacts the upper shell 6. The domes 38, 40 protrude about 0.225 inches above the surface of the seal 2. The seal 2 has a generally oval shape with two rounded portions 56, 58 on either side of the seal 2. The seal 2 also has an area 78 where the shape is concave instead of a smooth, convex arc. This concave area 78 can better accommodate the contours of the face of a user between the upper lip and the base of the nose. This slightly concave portion is reflected in other components of certain embodiments. For example, referring to FIG. 1B, a concave portion 80, 82, 84 of the upper shell 6, lower shell 8, and retainer 10, respectively, is shown. Each side of the seal 2 is shown bent at about a 15 degree angle ∝, β from planar. However, depending upon a particular user, the seal can be bent, as well as the shell 6, 8 and malleable element 4, at a variety of angles to suit a particular user's facial contours and the position of a user's nares.

Figure 9:
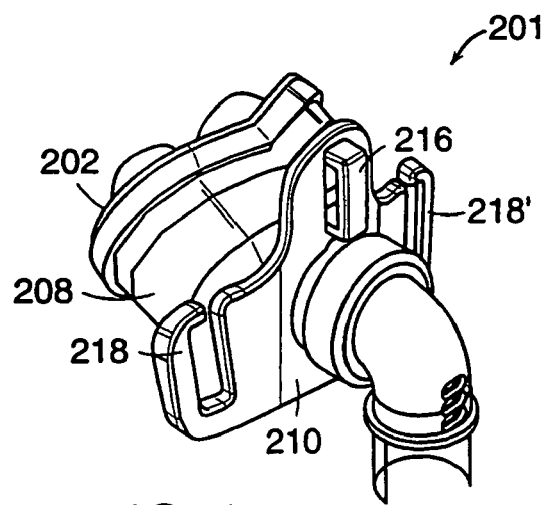
FIG. 9 is a schematic perspective view of an alternative embodiment of the invention.
Figure 10A:
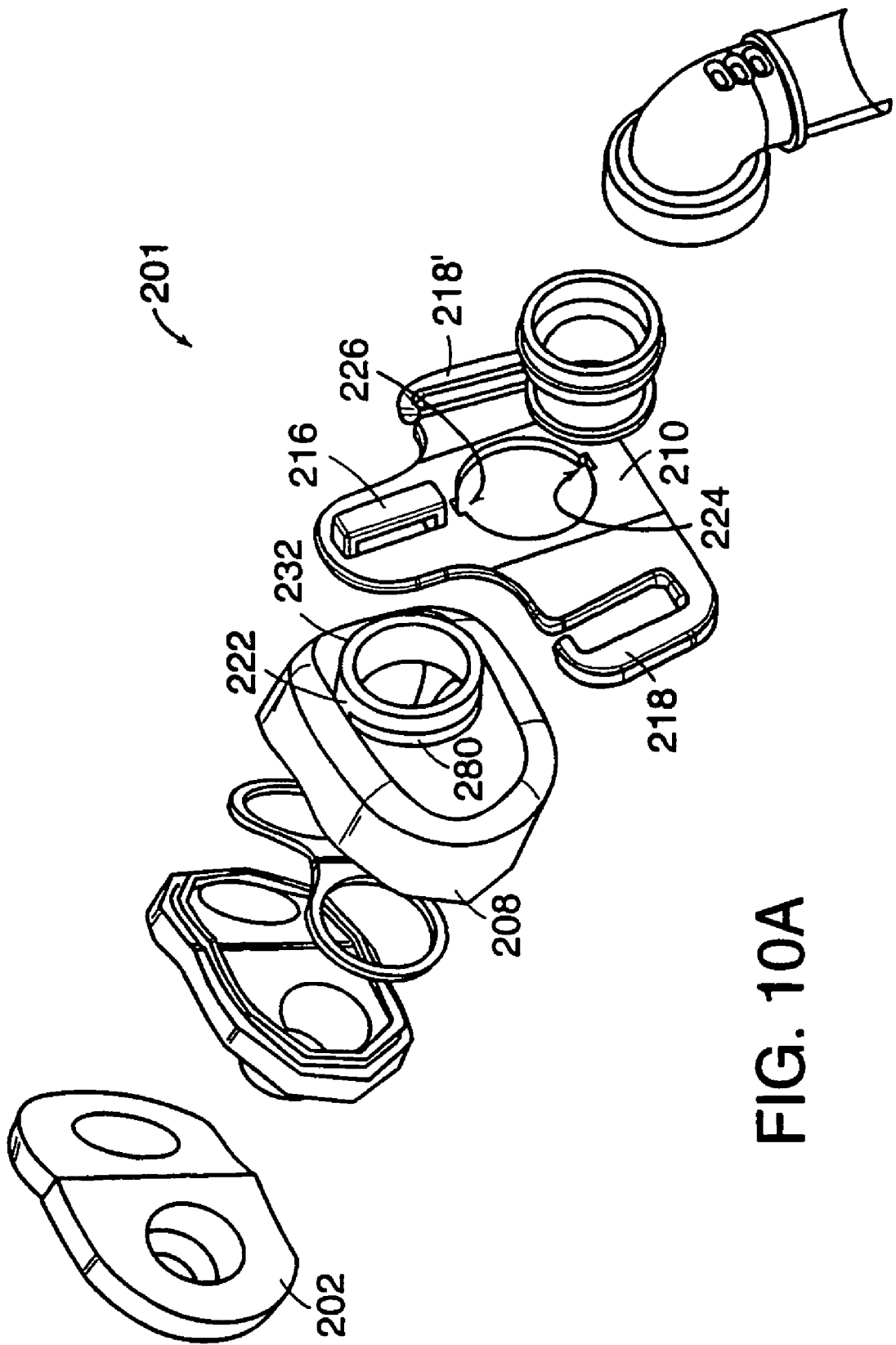
FIG. 10A is a schematic exploded perspective view of the embodiment depicted in FIG. 9.
Figure 10B:
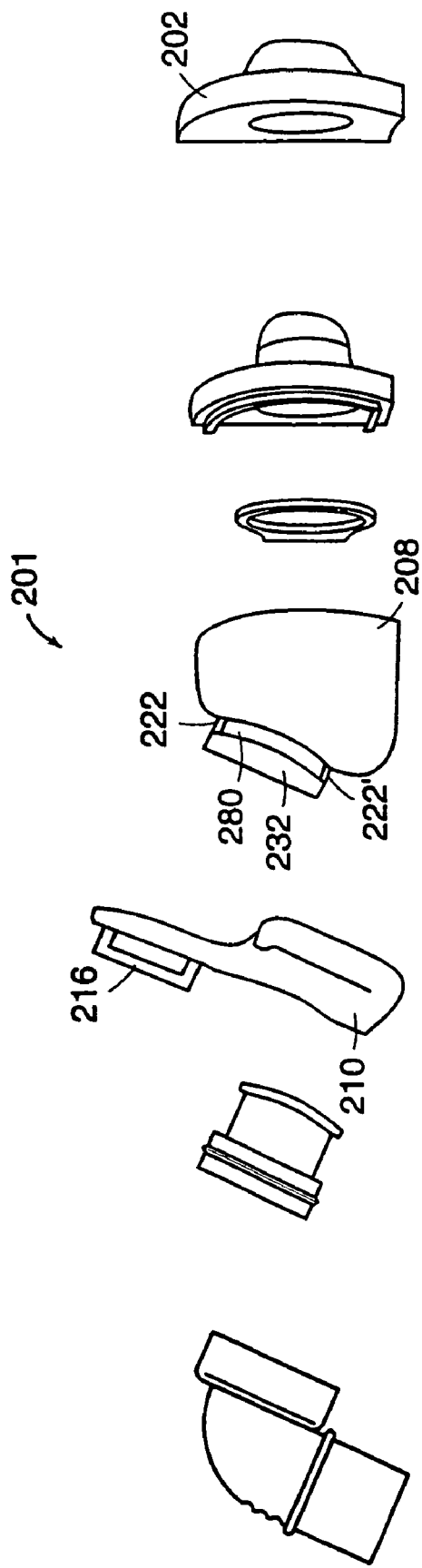
FIG. 10B is a schematic exploded side view of the components of the embodiment depicted in FIG. 9.
Figure 11:
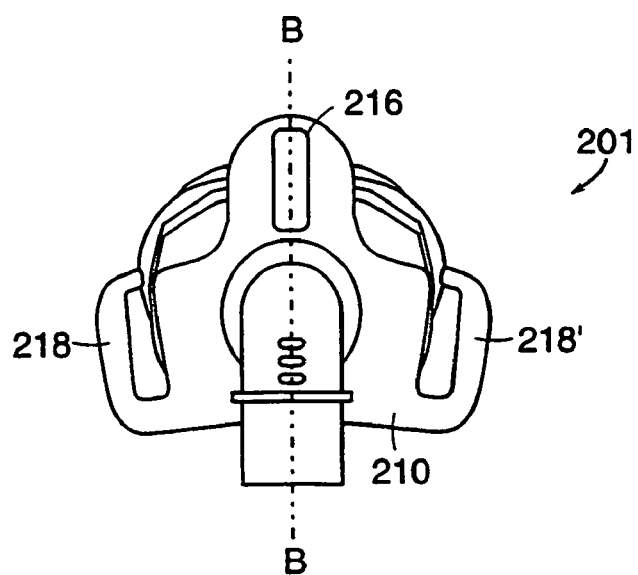
FIG. 11 is a schematic front view of the nasal mask of FIG. 9.

Now referring to FIGS. 9–11, an alternative embodiment of a nasal mask 201 has many, but not all, of the features of the nasal mask 1 embodiment shown in FIGS. 1–8C. Two differences between this alternative nasal mask 201 embodiment and the nasal mask 1 embodiment shown in FIGS. 1–8C are, respectively, that a retainer 210 connects to an inlet 232 in a different manner than the retainer 10 connects to the inlet 32 and that the retainer 210 is configured differently than the retainer 10.

The retainer 210 is disposed about the inlet 232 to facilitate retention of the mask 201 on a user. Two tabs 222, 222' included on the inlet 232 mate with two slots 226, 224 formed in the retainer 210 in a particular angular orientation. The retainer 210 has three connection points disposed remotely from the inlet 232, two lower connection points 218, 218' and one upper connection point 216. The nasal mask 201 is substantially symmetrical, as best seen in FIG. 11. Typically, the tabs 222, 222' hold the retainer 210 in an orientation such that the upper connection point 216 is above the lower connection points 218, 218' and all connection points 216, 218, 218' are disposed symmetrically about a vertical centerline B—B of the mask 201. Also, a depressed annular region 280 on the inlet 232 mates with the edges of an aperture passing through the retainer 210. The retainer aperture and the inlet 232 are generally sized in an interference fit so that the retainer 210 is properly retained by the cooperation of the tabs 222, 222', the slots 226, 224, and the depressed annular region 280 when fully seated against a lower shell 208. The depressed annular region 280 does not completely encircle the inlet 232, thus forming the two tabs 222, 222'. The retainer 210 can be constructed from, for example, but without limitation, a polycarbonate material.

The connection points 216, 218, 218' form slots which allow for connection of the retainer 210 with straps of a headgear apparatus below. A three point restraining system permits the nasal mask 201 to be securely and gently biased against the nares of a user. The lower connection points 218, 218' in concert with retention straps, generally maintain the nasal mask 201 against a user's face. The seal 202 rests against the external skin at the base of a user's nose and/or along the rim of the nares (the "naric area"). The upper connection point 216 in concert with an upper retention strap provides additional retention force on the upper portion of the nasal mask 201, closest to a user's eyes. This additional force retains the nasal mask 201 securely against the external skin surrounding the nares at the base of a user's nose and/or along the rim of a user's nares. The upper retention strap passes slidably through the upper connection point 216, best seen in FIG. 10B, and this single strap connects to other portions of a headgear apparatus. The upper retention strap is configured and oriented so as not to block the vision of a user.

In use, a user loops each of the lower retention straps through respective slots in each of the lower connection points 218, 218'. A hook and loop fastener system can be used to maintain the straps at a desired adjustment. The loops may be located along the majority of the lengths of the straps to provide a wide range of adjustment, with the hooks being located on the distal tip portions of the straps, such that when the distal tip of a strap is passed through a slot in a connector, the strap folds over on itself and the hooks engage the loops. Once the straps are adjusted, a user can slip the pre-formed loop into and out of the lower connection points 218, 218' at a notch that is cut into an edge of each of the lower connections points 218, 218'. The notch typically is removed from a portion of the lower connection points 218, 218' towards the centerline of the nasal mask 201 (line B—B in FIG. 11). Removing a notch from this portion allows the straps to be engaged and disengaged with the retainer 210 easily, while at the same time minimizes the possibility that the straps will slip out of their respective lower connection points 218, 218' while the nasal mask 201 is in use. Further, once the straps are adjusted a first time, they need not be adjusted again, merely being slipped out of the lower connection points 218, 218' by the notches.

Figure 12:
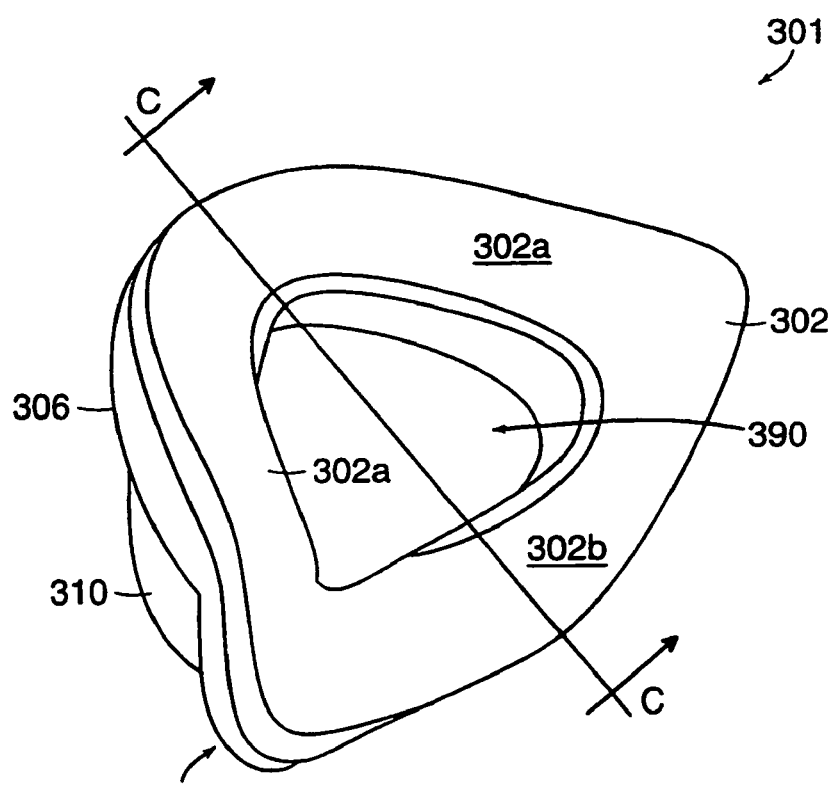
FIG. 12 is a schematic perspective view of another alternative embodiment of the invention.
Figure 13:
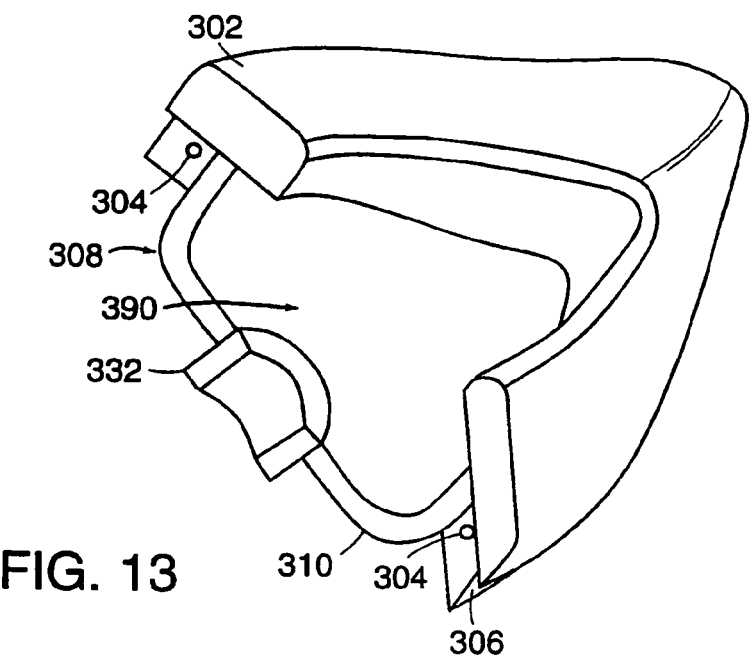
FIG. 13 is a schematic cross-sectional view of the embodiment depicted in FIG. 12 taken along line C—C of FIG. 12.
Figure 14:
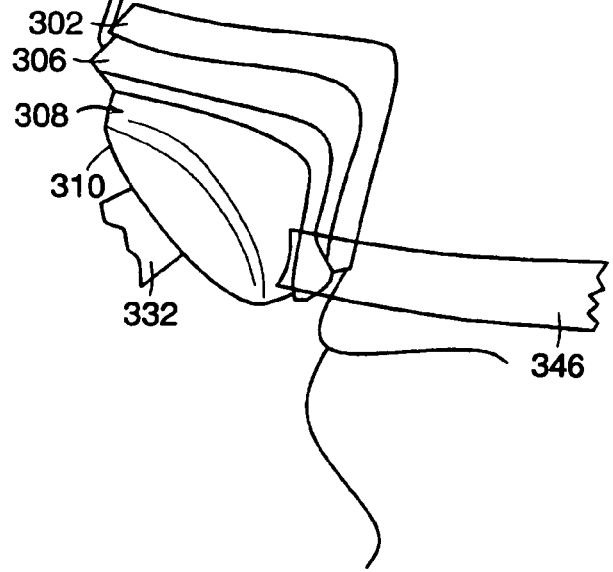
FIG. 14 shows a user donning the nasal mask of FIG. 12.

Now referring to FIGS. 12–14, another alternative embodiment of a nasal mask 301 is shown, which has similar components to those described above. The nasal mask 301 includes a soft seal 302 affixed to a shell 308, for example by bonding. The shell 308 includes a convex portion 310 and a flange 306. The seal 302 is affixed to the flange 306. Bonding agents and alternative means to affix the seal 302 to the shell 308 are described in more detail, above. The shell 308, typically is manufactured from a flexible material by a molding process. The shell 308 has a generally triangular shape that also is convex and is contoured such that a chamber 390 is formed by the sides of the shell 308 and the convex portion 310 of the shell 308. When in fluidic communication with a source of breathable gas, the chamber 390 contains the breathable gas. The gas in the chamber 390 is available to the user donning the nasal mask 301, and the gas, typically, is pressurized such that the gas is forced in to the user's airway, holding open the airway. The chamber 390 is substantially leakage-free due to the bond or interface between the seal 302 and the shell 308 as well as the conformance of the seal 302 against a user's skin.

Disposed within a perimeter portion of the shell 308, such as the flange 306, is a malleable element 304, best seen in FIG. 13. In this embodiment, the malleable element 304 is a wire made from a relatively soft metal, such as aluminum or copper, disposed about the opening of and within the flange 306 of the shell 308. Alternatively, the malleable element 304 can be affixed to a surface of the shell 308. The malleable element 304 can be constructed from any material that is formable and is capable of retaining the shape into which it is formed against the force of, for example, the flexible shell 308 trying to regain its memory shape. The combination of the compliant and resilient shell 308 and the malleable element 304, having sufficient rigidity to hold the shell 308 in a selected configuration, produces a "custom-fit" as desired by a particular user. Because the shell 308 is compliant, the perimeter and overall configuration of the opening of shell 308 can be reformed repeatedly, as necessary, by a particular user.

The nasal mask 301 also forms an inlet 332 in the shell 308 through which a breathable gas enters the chamber 390. A headgear apparatus retains the nasal mask 301 in the proper orientation against a user's naric area. The apparatus can include a retainer with other components, as described above, or the apparatus can be integral with the nasal mask 301. The apparatus connects to the nasal mask 301 either directly, or indirectly, through a retainer, with a strap 346 (only one is shown and labeled) positioned at either side of the upper lip. The straps 346 are directed to the nape of the neck, below the ears, of a user donning the nasal mask 301. A third strap 344 connects with the nasal mask 301 either directly, or indirectly, through a retainer, and is directed from the tip of the nose, between the eyes, and over the head of a user donning the nasal mask 301. The nasal mask 301 is maintained comfortably in sealing relation with the user's naric area with the headgear apparatus. This restraining system permits the nasal mask 301 to be securely and gently biased against a user's naric area. More particularly, the seal 302 is in contact with the external skin proximate the nares at the base of the user's nose. A chevron-shaped section 302a of the seal 302 seals against the base of the nose, from the tip along each side, and another section 302b of the seal 302 seals against the area above the upper lip or at the upper lip itself. As such, the chamber 390 is positioned immediately outside the user's nostrils and encloses the space between the edge of the base of the user's nose, proximate the nares, and the general area of the upper lip, best shown in FIG. 14. The soft seal 302 has the features of soft seals described above, allowing for a comfortable and air-tight seal about the user's naric area. Additionally, the positioning of the seal obviates any pressure that otherwise might be applied to the bridge of the nose in other designs.

The seal itself, in some embodiments, is about 0.25 inches (0.64 cm) to about 0.375 inches (0.953 cm) in depth and, at the contact point between the seal and a user's skin, is about 0.25 inches (0.64 cm) to about 0.375 inches (0.953 cm) in width. Also, in certain embodiments, the shell is a flexible thermoplastic elastomer, such as polyurethane or vinyl compounds, and is about 1.1 inches (2.8 cm) to about 1.7 inches (4.3 cm) at its widest point. This width is generally the width of a human's nasal area as measured from the outer edge of one naris to the outer edge of the other naris, although any shell width that fits generally within a human's nasal area is acceptable. For example, but without limitation, these dimensions can be increased or decreased by about 10%. The shell also is shaped to fit within the naric area. Some relevant dimensions for sizing the shell and seal include the length of the philtrum (generally about 0.4 inches (1.0 cm) to about 0.8 inches (2.0 cm)) as well as the amount to which a nose protrudes (generally about 0.7 inches (1.8 cm) to about 1.2 inches (about 3.0 cm)). Also, the chamber, in certain embodiments, at its widest point, is slightly smaller than the width of the shell.

Variations, modifications, and other implementations of what is described herein will occur to those of ordinary skill in the art without departing from the spirit and the scope of the invention as claimed. Accordingly, the invention is to be defined not by the preceding illustrative description, but instead by the spirit and scope of the following claims.

What is claimed is:

1. A nasal mask comprising:
   a shell forming a chamber having an inlet and an outlet with a perimeter;
   a malleable element disposed around the entirety of said perimeter and only around said perimeter, said malleable element formable and capable of holding said shell in a selected configuration to produce a desired fit for a user; and
   a seal disposed proximate the outlet, said seal dimensioned and shaped to contact and seal with external skin around both nares at a base of a nose of said user donning the mask, wherein substantially all of the sealing occurs between the seal and the external skin.

2. The nasal mask of claim 1 wherein said malleable element comprises a wire made of a relatively soft metal.

3. The nasal mask of claim 1 wherein said malleable element is disposed within the shell.

4. The nasal mask of claim 1 wherein the seal comprises a bladder.

5. The nasal mask of claim 4 wherein the bladder is filled with silicone gel.

6. The nasal mask of claim 5 wherein the gel is molded in a predetermined configuration.

7. The nasal mask of claim 1 wherein the seal is bonded to the shell.

8. The nasal mask of claim 1 further comprising a conduit attached to the inlet.

9. The nasal mask of claim 8 wherein the conduit comprises an angled portion.

10. The nasal mask of claim 8 wherein the conduit comprises a rotary connection.

11. The nasal mask of claim 8 wherein the conduit comprises a ball and socket connection.

12. The nasal mask of claim 1 further comprising a headgear apparatus attached to the mask for retaining the mask on a user.

* * * * *